United States Patent
Laricchia et al.

(10) Patent No.: US 9,522,861 B2
(45) Date of Patent: Dec. 20, 2016

(54) METHODS AND APPARATUSES FOR PRODUCING LOW SULFUR PROPANE AND BUTANE

(71) Applicant: UOP LLC, Des Plaines, IL (US)

(72) Inventors: Luigi Laricchia, Arlington Heights, IL (US); Jonathan Andrew Tertel, Mt. Prospect, IL (US)

(73) Assignee: UOP LLC, Des Plaines, IL (US)

( * ) Notice: Subject to any disclaimer, the term of this patent is extended or adjusted under 35 U.S.C. 154(b) by 419 days.

(21) Appl. No.: 14/083,116

(22) Filed: Nov. 18, 2013

(65) Prior Publication Data

US 2015/0141728 A1 May 21, 2015

(51) Int. Cl.

| C07C 7/148 | (2006.01) |
|---|---|
| C07C 7/152 | (2006.01) |
| C10G 19/02 | (2006.01) |
| C10G 19/08 | (2006.01) |
| C07C 7/10 | (2006.01) |
| C07C 7/00 | (2006.01) |

(52) U.S. Cl.
CPC ........ *C07C 7/10* (2013.01); *C07C 7/005* (2013.01)

(58) Field of Classification Search
CPC ......... C07C 7/148; C07C 7/152; C10G 19/02; C10G 19/08
USPC ........ 585/802, 853, 854; 208/226, 227, 228, 208/229, 235
See application file for complete search history.

(56) References Cited

U.S. PATENT DOCUMENTS

| 2,064,999 A | 12/1936 | Watson |
| 2,437,348 A | 3/1948 | Brown et al. |
| 2,556,157 A | 6/1951 | Brown et al. |
| 2,733,190 A | 1/1956 | Noble |
| 2,908,626 A | 10/1959 | Poll |
| 4,562,300 A | 12/1985 | LaFoy |
| 4,897,098 A | 1/1990 | Pate et al. |
| 5,146,039 A | 9/1992 | Wildt et al. |
| 5,360,532 A | 11/1994 | Fletcher et al. |
| 5,424,051 A * | 6/1995 | Nagji ................. B01D 53/04 423/234 |
| 5,597,476 A | 1/1997 | Hearn et al. |
| 6,623,627 B1 | 9/2003 | Zhou |
| 7,342,145 B2 | 3/2008 | Wu et al. |
| 7,445,702 B2 | 11/2008 | Abbott |

(Continued)

FOREIGN PATENT DOCUMENTS

| WO | 2005019387 A1 | 3/2005 |
| WO | 2005121279 A1 | 12/2005 |
| WO | 2012066572 A2 | 5/2012 |

OTHER PUBLICATIONS

Search Report dated Jan. 19, 2015 for corresponding PCT Appl. No. PCT/US2014/061866.

*Primary Examiner* — Thuan D Dang

(57) ABSTRACT

Methods and apparatuses are provided for producing low sulfur propane and butane. The method includes reacting a mercaptan in a washed feed stream with a caustic stream to produce a mercaptan salt in a rich caustic stream and a hydrocarbon treated stream. The mercaptan salt in the rich caustic stream is reacted with oxygen and water to produce a mixed caustic/disulfide stream, and the caustic and disulfides in the mixed caustic/disulfide stream are separated to produce a disulfide stream and the caustic stream. The hydrocarbon treated stream is fractionated to produce a propane stream, a butane stream, and a C5+ stream.

7 Claims, 2 Drawing Sheets

(56) References Cited

U.S. PATENT DOCUMENTS

2012/0000827 A1   1/2012   Krupa et al.

* cited by examiner

METHODS AND APPARATUSES FOR
PRODUCING LOW SULFUR PROPANE AND
BUTANE

TECHNICAL FIELD

The present disclosure generally relates to methods and apparatuses for producing propane and butane, and more particularly relates to methods and apparatuses for producing propane and butane without sulfur containing compounds.

BACKGROUND

Hydraulic fracturing of shale, commonly known as "fracking," allows recovery of hydrocarbons trapped in the shale. The recovered hydrocarbons often have 1 to about 5 or more carbon atoms (referred to as C1-5+, where "C" refers to carbon, and the following number refers to the number of carbon atoms in the molecule), as well as sulfur containing compounds and other impurities. The recovered hydrocarbons are typically sent to a processing plant and fractionated into products based on the number of carbon atoms in the molecules of the product, such as natural gas (with methane and ethane), propane, butane, and pentane. The sulfur-containing compounds are removed from the products after fractionation, and the products are then further processed and/or sold. Each sulfur removal process requires capital expense for the equipment, as well as ongoing operating costs.

Accordingly, it is desirable to develop methods and systems for producing sulfur free propane, butane, and other hydrocarbon products from hydraulic fracturing processes and other C1-5+ streams. In addition, it is desirable to develop methods and systems for producing sulfur free hydrocarbon products with a reduced number of sulfur removal units. Furthermore, other desirable features and characteristics of the present embodiment will become apparent from the subsequent detailed description and the appended claims, taken in conjunction with the accompanying drawings and this background.

BRIEF SUMMARY

Methods and apparatuses for producing low sulfur propane and butane are provided. In an exemplary embodiment, a method includes reacting a mercaptan in a washed feed stream with a caustic stream to produce a mercaptan salt in a rich caustic stream and a hydrocarbon treated stream. The mercaptan salt in the rich caustic stream is reacted with oxygen and water to produce a mixed caustic/disulfide stream, and the caustic and disulfides in the mixed caustic/disulfide stream are separated to produce a disulfide stream and the caustic stream. The hydrocarbon treated stream is fractionated to produce a propane stream, a butane stream, and a C5+ stream.

In accordance with another exemplary embodiment, a method for producing low sulfur propane and butane includes feeding a washed feed stream into an extraction unit to produce a hydrocarbon treated stream and a rich caustic stream, where the mercaptan in the washed feed stream is reacted with the caustic to produce a mercaptan salt that remains in the rich caustic stream. The mercaptan salt is removed from the rich caustic stream in an oxidizer to produce a caustic stream that is fed into the extraction unit.

In accordance with a further exemplary embodiment, an apparatus for producing low sulfur propane and butane includes an extraction unit configured to react a mercaptan with caustic to produce a hydrocarbon treated stream and a rich caustic stream. A caustic regeneration unit is fluidly coupled to the extraction unit, where the caustic regeneration unit is configured to react a mercaptan salt with oxygen and water to produce a disulfide. A hydrocarbon fractionation zone is also fluidly coupled to the extraction unit, and configured to fractionate hydrocarbons with 3 to 5+ carbon atoms into a propane stream, a butane stream, and a C5+ stream.

BRIEF DESCRIPTION OF THE DRAWINGS

The present embodiment will hereinafter be described in conjunction with the following drawing figures, wherein like numerals denote like elements, and wherein.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to methods and apparatuses for producing a propane product and a butane product, as well as a C5+ product from a C1-5+ feed stream. The C1-5+ feed stream is fractionated to remove light gases having 1 to 2 carbons atoms and provide a C3-5+ stream. In some embodiments, the C1-5+ stream is produced from hydraulic fracturing, but the C1-5+ stream may also be provided from a petroleum refinery process or other sources. The C3-5+ feed stream includes sulfur compounds, such as hydrogen sulfide and mercaptans. The hydrogen sulfide is removed with an amine absorber or caustic prewash. The mercaptans are heavier than the C1-2 products, so they remain in the C3-5+ stream when the light gases are removed. The C3-5+ stream is a feed stream that is contacted with an aqueous caustic solution in an extraction unit to produce water soluble mercaptan salts from the mercaptans. This produces a rich caustic stream with the mercaptan salts and an essentially mercaptans-free hydrocarbon treated stream, where the C1 to C3 mercaptan concentration is less than about 5 parts per million by weight (ppm). The mercaptan salts in the rich caustic stream are oxidized with oxygen and water in the presence of an oxidizing catalyst to produce disulfides and caustic. The disulfides are not soluble in water, so they are separated from the caustic by a simple split and the recovered caustic is returned to the extraction unit. The C3-5+ feed stream is fractionated to produce a propane stream, a butane stream, and a C5+ stream. A low level of disulfides may be returned to the extraction unit in the recovered caustic. The disulfides have high boiling points, so they remain with a C5+ bottoms stream after fractionation. The disulfides are optionally removed from the C5+ stream in a later processing step, but the propane (C3) and butane (C4) streams are sulfur free. This reduces the number of sulfur extraction units needed to process the C1-5+ stream, because a single sulfur extraction unit upstream from the C3-5+ fractionation process replaces the multiple sulfur extraction units used for each stream exiting the C3-5+ fractionation process.

Figure 1:
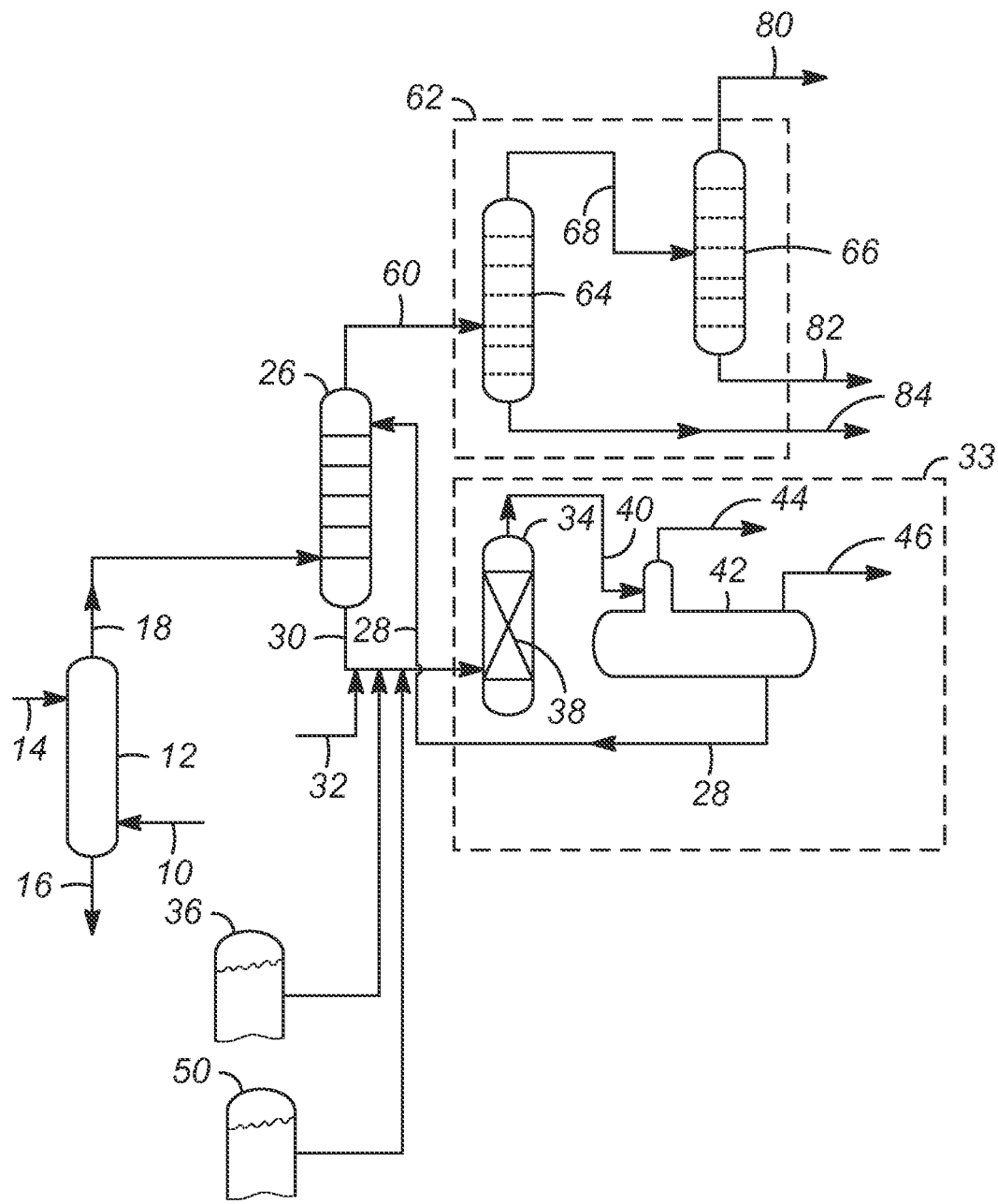
FIG. 1 is a schematic diagram of an exemplary embodiment of an apparatus and a method for producing a propane stream, a butane stream, and a C5+ stream.

Reference is now made to FIG. 1. A feed stream 10 is provided, where the feed stream 10 includes hydrocarbons with 3 to 5 carbons, and possibly low concentrations of hydrocarbons with 6 or more carbon atoms. The feed stream 10 also includes sulfur containing compounds, such as hydrogen sulfide and various mercaptans. In one embodiment, the feed stream 10 is a product of hydraulic fracturing. Hydraulic fracturing allows extraction of hydrocarbons previously trapped in shale, rock, or other geological formations. Hydraulic fracturing creates cracks in the shale, rock, or other structure, and small proppants such as sand or aluminum oxide are used to maintain the cracks in an open position. The hydrocarbons can then flow through the cracks for extraction. Most hydrocarbons extracted with hydraulic fracturing are primarily (90 mass percent or more) C1-5 hydrocarbons, but other materials are also present, such as hydrocarbons with 6 or more carbon atoms, hydrogen sulfide, mercaptans, radium, carbon dioxide, nitrogen, and traces of noble gases. It is desirable to remove the hydrogen sulfide and mercaptans because they are often toxic, have a strong smell, may have sulfur concentrations that are limited by governmental regulations, and can cause corrosion. The C1-5 hydrocarbons are fractionated to produce a C1-2 light gases stream and a C3-5+ stream, and the C3-5+ stream is then fed into the process as the feed stream 10.

The feed stream 10 is introduced to a prewash unit 12 for prewashing. Several different types of prewash units 12 can be used, including caustic washing, amine treatment, and sodium carbonate treatment units. In an exemplary embodiment, the prewash unit 12 intimately mixes the feed stream 10 with a prewash stream 14, where the prewash stream 14 is an aqueous caustic (e.g., sodium hydroxide) solution at a concentration of from about 5 weight percent (wt. %) about 15 wt. % caustic in water. The caustic reacts with the hydrogen sulfide to produce sodium hydrosulfide and sodium sulfide, both of which are soluble in water and remain in the prewash stream 14. A washed feed stream 18 containing hydrocarbons and a spent prewash stream 16 containing the prewash material and reaction products, such as caustic and sodium hydrosulfide, exit the prewash unit 12. The caustic in the prewash unit 12 is gradually discharged and replaced with fresh caustic. Operating conditions for the prewash unit 12 are variable, but typically include ambient temperatures and pressures sufficient to keep the feed stream 10 liquid. For example, temperatures from about 10 degrees centigrade (° C.) to about 60° C., and more typically about 30 to about 50° C. and pressures ranging from about 5 atmosphere to about 30 atmospheres can be used.

Next, the washed feed stream 18 is treated in an extraction unit 26 to remove any remaining mercaptans by reacting them with caustic to produce mercaptan salts. The washed feed stream 18 is intimately contacted with a caustic stream 28, where the washed feed stream 18 and the caustic stream 28 are in the liquid phase. In an exemplary embodiment, the caustic stream 28 is charged near the top of the extraction unit 26, and the washed feed stream 18 is charged near the bottom of the extraction unit 26. The concentration of the caustic stream 28 varies, but typically ranges from about 5 to about 25 wt. % caustic in water. The aqueous caustic stream 28 does not form a solution or a suspension with the hydrocarbons in the washed feed stream 18, and the caustic is more dense than the hydrocarbons in the washed feed stream 18. Therefore, the caustic flows downward through the extraction unit 26 as hydrocarbons in the washed feed stream 18 flow upward through the extraction unit 26. In one embodiment, the extraction unit 26 includes a plurality of trays configured to direct the heavier caustic stream 28 through a tortuous path downward while the washed feed stream 18 is directed through a tortuous path upward, and the trays are designed to intimately mix and contact the two streams as they flow in a counter-current manner. In an alternate embodiment, the extraction unit 26 includes packing or other structures to mix the caustic and hydrocarbons as they flow past each other. The extraction unit 26 is sized to provide sufficient stages to react the mercaptans with the caustic, such as about 2 to about 6 stages or more. Exemplary operating conditions for the extraction unit include a temperature of about 10° C. to about 60° C. and a pressure sufficient to keep the washed feed stream in the liquid phase, such as about 5 atmospheres to about 30 atmospheres.

A rich caustic stream 30 exits the extraction unit 26, and includes the aqueous caustic solution and mercaptan salts. An oxygen supply stream 32 is added to the rich caustic stream 30 to react with the mercaptan salts. In an exemplary embodiment, the oxygen supply stream 32 is air, but other oxygen-containing gases can also be used. Oxygen and water react with the mercaptan salts in an oxidizer 34 to form disulfides and caustic. An unaided reaction rate is slow, and therefore an oxidation catalyst 36 is used to speed the oxidation reaction to produce the disulfides, and the oxidation catalyst 36 is added to the caustic recirculation system on an as needed basis. In an exemplary embodiment, the oxidation catalyst 36 is added to the rich caustic stream 30 upstream from the oxidizer 34, but the oxidation catalyst 36 could be added at other locations as well.

The oxidation catalyst 36 is a metal chelate, and can be in liquid or solid form. Several chelating agents can be used, such as phthalocyanines, tetraphenylporphyrins, or tetraphyidinoporphyrazines. Many chelating agents are not ready soluble in water, but water solubility can be increased by brominating, sulfonating, or carboxilating the chelating agents. The metal is one or more of iron, cobalt, manganese, molybdenum, or vanadium. In some embodiments, water soluble oxidation catalysts 36 are used, but insoluble forms of the oxidation catalyst 36 can be used in suspension or supported on a substrate that is either held in a fixed position in the oxidizer 34, or maintained in a slurry with the caustic. Suitable substrates include activated carbon, charcoal granules, thermoplastic polymers, exchange resins, and a wide variety of other materials. One exemplary oxidation catalyst 36 is iron phthalocyanine tetrasulfonate, but many other embodiments of an oxidation catalyst 36 are possible.

The rich caustic stream 30 (including the mercaptan salts), oxygen from the oxygen supply stream 32, and the oxidation catalyst 36 are heated and enter the oxidizer 34. The oxidizer 34 includes a packed bed 38, trays, or other structures that keep the aqueous caustic solution and the water insoluble disulfides well mixed as the caustic flows through. The mercaptan salts are oxidized to disulfides, so essentially no mercaptans remain in a mixed caustic/disulfide stream 40 exiting the oxidizer 34. Exemplary operating conditions for the oxidizer 34 include a pressure of about 1 atmosphere to about 10 atmospheres, and a temperature of about 30° C. to about 60° C. The caustic stream 28 is replenished with fresh caustic 50 as needed. The fresh caustic 50 can be added in a wide variety of locations, including but not limited to the rich caustic stream 30 upstream from the oxidizer 34, as illustrated.

The mixed caustic/disulfide stream 40 exits the oxidizer 34 and enters the disulfide separator 42. The disulfide separator 42 has no agitation and has a sufficient volume to allow the water insoluble disulfides to split from the aqueous caustic solution. The oxidizer 34 and the disulfide separator 42 work together as a caustic regeneration unit 33 that is fluidly coupled to the extraction unit 26. In an exemplary embodiment, the disulfide separator 42 has a residence time of about of about 0.5 to about 3 hours. Any excess gases, such as excess nitrogen or oxygen from the oxygen supply stream 32, are vented from the disulfide separator 42 in a vent line 44. The vent line 44 can be directed to a scrubber or other pollution control device, and optionally includes a liquids entrainment separator (not illustrated) to prevent discharge of caustic or disulfides. The disulfide oil is less dense than the caustic, so the upper layer of disulfide oil exits near the top of the disulfide separator 42 in a disulfide stream 46, and the caustic stream 28 is recovered from near the bottom of the disulfide separator 42. The caustic stream 28 contains small amounts of carryover disulfide, and these disulfides enter the extraction unit 26 with the caustic stream 28. The carryover disulfides are then combined with the hydrocarbons exiting the extraction unit 26, because the disulfides are more soluble in the non-polar hydrocarbons than in the polar caustic solution.

Mercaptans are removed from the washed feed stream 18 in the extraction unit 26, and the hydrocarbons in the washed feed stream 18 exit the extraction unit 26 in a hydrocarbon treated stream 60. The hydrocarbon treated stream 60 also includes a low concentration of disulfides from the recovered caustic stream 28. The hydrocarbon treated stream 60 is fractionated in a hydrocarbon fractionation zone 62 to produce a propane stream 80, a butane stream 82, and a C5+ stream 84. The hydrocarbon fractionation zone 62 includes one or more fractionation units in various configurations. In an exemplary embodiment, the hydrocarbon fractionation zone 62 includes a debutanizer 64 and a depropanizer 66. The hydrocarbon treated stream 60 enters the debutanizer 64, which produces the C5+ stream 84 which exits at or proximate the bottom of the debutanizer 64 as a bottoms stream, and a C3-4 stream 68 which exits at or proximate the top of the debutanizer 64 as an overhead stream. The disulfides are relatively high boiling compounds, so any residual disulfides in the hydrocarbon treated stream 60 exit the debutanizer 64 (and the hydrocarbon fractionation zone 62) in the C5+ stream 84. The C5+ stream 84 can be used for gasoline blending or other purposes, and additional sulfur extraction or sweetening steps are optionally employed. Exemplary operating conditions for the debutanizer 64 include an operating pressure of from about 7 atmospheres to about 14 atmospheres, an overhead temperature from about 40° C. to about 90° C., and a bottoms temperature from about 150° C. to about 200° C.

The C3-4 stream 68 exits the debutanizer 64 and enters the depropanizer 66. The C3-4 stream 68 has effectively no sulfur compounds at this point, because hydrogen sulfide was removed in the prewash unit 12, mercaptans were removed in the extraction unit 26, and residual disulfides remain in the C5+ stream 84 discharged from the debutanizer 64. Therefore, there is no need for any further sulfur removal from the C3-4 stream 68, or any process streams downstream from the C3-4 stream 68. Positioning the extraction unit 26 upstream from the hydrocarbon fractionation zone 62 reduces the required number of extraction units 26 to produce sulfur free propane and butane, because separate extraction units are not needed downstream from the hydrocarbon fractionation zone 62. The depropanizer 66 separates the C3-4 stream 68 into the propane stream 80 and the butane stream 82, and the propane, butane, pentane, and larger hydrocarbons are then available for sale or further processing. Exemplary operating conditions for the depropanizer 66 include an operating pressure from about 15 atmospheres to about 20 atmospheres, an overhead temperature from about 35° C. to about 65° C., and a bottoms temperature from about 90° C. to about 120° C.

Figure 2:
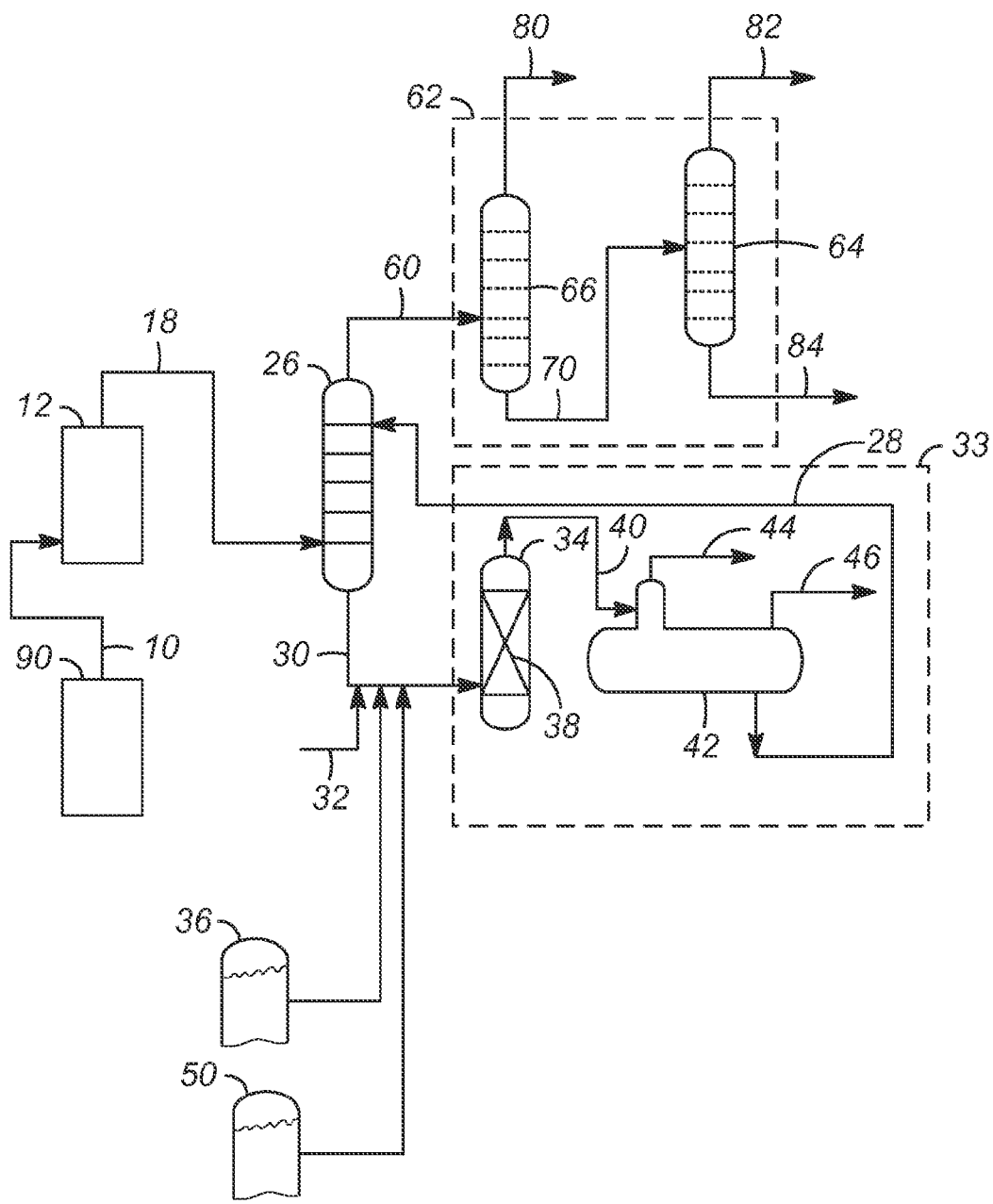
FIG. 2 is a schematic diagram of another exemplary embodiment of an apparatus and a method for producing a propane stream, a butane stream, and a C5+ stream.

Reference is now made to an alternate exemplary embodiment illustrated in FIG. 2. A petroleum processing facility 90 provides the feed stream 10, which is charged into the prewash unit 12. In this example, the feed stream 10 primarily includes 3 to 5 carbon atoms and sulfur compounds, so there is no need to remove light gases from the feed stream 10. In alternate embodiments with a broader range of hydrocarbons, the feed stream 10 is fractionated as described above. The caustic treatment steps for removing the sulfur containing compounds are similar to those described above, but the hydrocarbon fractionation zone 62 utilizes the depropanizer 66 upstream from the debutanizer 64. The depropanizer 66 produces the propane stream 80 and a C4-5+ stream 70, where the C4-5+ stream 70 includes the higher boiling disulfides. The C4-5+ stream 70 enters the debutanizer 64 and produces the butane stream 82 and the C5+ stream 84. The relatively high boiling disulfides remain in the C5+ stream 84, as described above, so there is no need for further sulfur removal processes for the propane stream 80, the butane stream 82, or any process downstream from them. Exemplary operating conditions for the depropanizer 66 and the debutanizer 64 are described above.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

The invention claimed is:

1. A method for producing low sulfur propane and butane, the method comprising the steps of:
    reacting, in the liquid phase, a mercaptan in a liquid phase washed feed stream containing hydrocarbon with a caustic stream to produce a mercaptan salt in a rich caustic stream and a hydrocarbon treated stream wherein the liquid phase washed feed stream is derived from hydraulic fracturing of shale;
    reacting the mercaptan salt in the rich caustic stream with oxygen and water to produce a mixed caustic/disulfide stream;
    separating caustic and disulfides in the mixed caustic/disulfide stream to produce a disulfide stream and the caustic stream; and
    fractionating the hydrocarbon treated stream by debutanizing the hydrocarbon treated stream to produce a C3-4 stream and the C5+ stream, and depropanizing the C3-4 stream to produce the propane stream and the butane stream.

2. The method of claim 1 further comprising:
    prewashing the liquid phase washed feed stream prior to reacting the mercaptan in the liquid phase washed feed stream with the caustic stream, wherein prewashing comprises contacting the washed feed stream with a prewash stream comprising sodium hydroxide wherein the prewashing is conducted in the liquid phase.

3. The method of claim 1 wherein reacting the mercaptan salt in the rich caustic stream with oxygen further comprises contacting the rich caustic stream with air.

4. The method of claim 1 wherein reacting the mercaptan salt in the rich caustic stream further comprises adding an oxidation catalyst to the rich caustic stream.

5. The method of claim 1 wherein reacting the mercaptan salt in the rich caustic stream further comprises adding an oxidation catalyst to the rich caustic stream wherein the oxidation catalyst is in liquid form, and wherein the oxidation catalyst comprises a metal chelate.

6. The method of claim 1 wherein reacting the mercaptan in the washed feed stream with the caustic stream further comprises reacting the mercaptan in the washed feed stream with the caustic stream wherein 90 mass percent or more of the washed feed stream comprises hydrocarbons with 3 to 5 carbon atoms.

7. The method of claim 1 further comprising:
replenishing the caustic stream with fresh caustic.

* * * * *